United States Patent
Li et al.

(10) Patent No.: US 9,561,098 B2
(45) Date of Patent: Feb. 7, 2017

(54) INTRAOCULAR LENS THAT MATCHES AN IMAGE SURFACE TO A RETINAL SHAPE, AND METHOD OF DESIGNING SAME

(71) Applicant: Abbott Medical Optics Inc., Santa Ana, CA (US)

(72) Inventors: Kaccie Y. Li, Groningen (NL); Hendrik A. Weeber, Groningen (NL); Carmen Canovas Vidal, Groningen (NL); Patricia Ann Piers, Groningen (NL); Huawei Zhao, Irvine, CA (US); Robert Rosén, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 91 days.

(21) Appl. No.: 14/196,762

(22) Filed: Mar. 4, 2014

(65) Prior Publication Data

US 2014/0253877 A1    Sep. 11, 2014

Related U.S. Application Data

(60) Provisional application No. 61/776,184, filed on Mar. 11, 2013.

(51) Int. Cl.
*A61B 3/10* (2006.01)
*A61B 3/00* (2006.01)
*A61F 2/16* (2006.01)
*A61B 3/107* (2006.01)

(52) U.S. Cl.
CPC ........... *A61F 2/1637* (2013.01); *A61B 3/0025* (2013.01); *A61B 3/107* (2013.01); *A61F 2/1613* (2013.01); *A61F 2/1648* (2013.01); *A61F 2250/0053* (2013.01)

(58) Field of Classification Search
USPC .................................................. 351/212, 246
See application file for complete search history.

(56) References Cited

U.S. PATENT DOCUMENTS

| | | | |
|---|---|---|---|
| 3,367,734 | A | 2/1968 | Bystricky et al. |
| 4,581,031 | A | 4/1986 | Koziol et al. |
| 4,637,697 | A | 1/1987 | Freeman |
| 4,642,112 | A | 2/1987 | Freeman |
| 4,648,878 | A | 3/1987 | Kelman |
| 4,655,565 | A | 4/1987 | Freeman |
| 4,666,446 | A | 5/1987 | Koziol et al. |
| 4,778,462 | A | 10/1988 | Grendahl |
| 4,795,462 | A | 1/1989 | Grendahl |

(Continued)

FOREIGN PATENT DOCUMENTS

| | | |
|---|---|---|
| EP | 0343067 A1 | 11/1989 |
| EP | 0457553 A2 | 11/1991 |

(Continued)

OTHER PUBLICATIONS

Atchison D.A., et al., "Shape of the Retinal Surface in Emmetropia and Myopia," Investigative Ophthalmology & Visual Science, 2005, vol. 46 (8), pp. 2698-2707.

(Continued)

*Primary Examiner* — Jack Dinh
(74) *Attorney, Agent, or Firm* — Abbott Medical Optics Inc.

(57) ABSTRACT

An intraocular lens (IOL), system, and method having a base lens and a complementary lens selected to form a curved image surface matching a retina surface when placed in an eye's line of sight.

9 Claims, 5 Drawing Sheets

(56) References Cited

U.S. PATENT DOCUMENTS

| | | |
|---|---|---|
| 4,798,608 A | 1/1989 | Grendahl |
| 4,798,609 A | 1/1989 | Grendahl |
| 4,828,558 A | 5/1989 | Kelman |
| 4,932,970 A | 6/1990 | Portney |
| 4,995,714 A | 2/1991 | Cohen |
| 4,995,715 A | 2/1991 | Cohen |
| 5,016,977 A | 5/1991 | Baude et al. |
| 5,056,908 A | 10/1991 | Cohen |
| 5,066,301 A | 11/1991 | Wiley |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,144,483 A | 9/1992 | Cohen |
| 5,225,858 A | 7/1993 | Portney |
| 5,229,797 A | 7/1993 | Futhey et al. |
| 5,354,334 A | 10/1994 | Fedorov et al. |
| 5,652,638 A | 7/1997 | Roffman et al. |
| 5,683,457 A | 11/1997 | Gupta et al. |
| 5,699,142 A | 12/1997 | Lee et al. |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,968,094 A | 10/1999 | Werblin et al. |
| 6,126,283 A | 10/2000 | Wen et al. |
| 6,126,286 A | 10/2000 | Portney |
| 6,142,625 A | 11/2000 | Sawano et al. |
| 6,183,084 B1 | 2/2001 | Chipman et al. |
| 6,197,057 B1 | 3/2001 | Peyman et al. |
| 6,210,005 B1 | 4/2001 | Portney |
| 6,338,559 B1 | 1/2002 | Williams et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,609,793 B2 | 8/2003 | Norrby et al. |
| 6,705,729 B2 | 3/2004 | Piers et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,913,620 B2 | 7/2005 | Lipshitz |
| 6,923,539 B2 | 8/2005 | Simpson et al. |
| 6,923,540 B2 | 8/2005 | Ye et al. |
| 6,986,578 B2 | 1/2006 | Jones |
| 7,025,456 B2 | 4/2006 | Morris et al. |
| 7,025,460 B2 | 4/2006 | Smitth, III |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,186,266 B2 | 3/2007 | Peyman |
| 7,188,949 B2 | 3/2007 | Bandhauer et al. |
| 7,238,201 B2 | 7/2007 | Portney et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,410,500 B2 | 8/2008 | Claoue |
| 7,441,894 B2 | 10/2008 | Zhang et al. |
| 7,475,986 B2 | 1/2009 | Dai et al. |
| 7,503,655 B2 | 3/2009 | Smith, III |
| 7,615,073 B2 | 11/2009 | Deacon et al. |
| 7,665,842 B2 | 2/2010 | Ho et al. |
| 7,766,482 B2 | 8/2010 | Smith, III et al. |
| 7,871,162 B2 | 1/2011 | Weeber |
| 7,997,727 B2 | 8/2011 | Ho et al. |
| 8,057,034 B2 | 11/2011 | Ho et al. |
| 8,062,361 B2 | 11/2011 | Nguyen et al. |
| 8,201,943 B2 | 6/2012 | Hammer et al. |
| 8,206,442 B2 | 6/2012 | Sel et al. |
| 8,262,728 B2 | 9/2012 | Zhang et al. |
| 8,430,508 B2 | 4/2013 | Weeber |
| 8,540,365 B2 | 9/2013 | Varnas |
| 8,862,447 B2 | 10/2014 | Weeber |
| 9,345,570 B2 | 5/2016 | Sieber et al. |
| 2002/0101564 A1 | 8/2002 | Herrick |
| 2002/0105617 A1 | 8/2002 | Norrby et al. |
| 2002/0118337 A1 | 8/2002 | Perrott et al. |
| 2003/0076478 A1 | 4/2003 | Cox |
| 2003/0171808 A1 | 9/2003 | Phillips |
| 2004/0021824 A1 | 2/2004 | Ye et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0230299 A1 | 11/2004 | Simpson et al. |
| 2005/0096226 A1 | 5/2005 | Stock et al. |
| 2005/0128432 A1 | 6/2005 | Altmann |
| 2005/0203619 A1 | 9/2005 | Altmann |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0058874 A1 | 3/2006 | Peli |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0158611 A1 | 7/2006 | Piers et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0247766 A1 | 11/2006 | Marin |
| 2007/0052920 A1 | 3/2007 | Stewart et al. |
| 2007/0093891 A1 | 4/2007 | Tabernero et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0198083 A1 | 8/2007 | Sel et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0269883 A1 | 10/2008 | Das et al. |
| 2008/0269885 A1 | 10/2008 | Simpson et al. |
| 2008/0269886 A1 | 10/2008 | Simpson et al. |
| 2008/0269890 A1 | 10/2008 | Simpson et al. |
| 2008/0312738 A1 | 12/2008 | Wanders |
| 2009/0018652 A1 | 1/2009 | Hermans et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0198326 A1 | 8/2009 | Zhou et al. |
| 2009/0204211 A1 | 8/2009 | Angelopoulos et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0292354 A1 | 11/2009 | Gontijo et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0100177 A1 | 4/2010 | Zhao |
| 2010/0100178 A1 | 4/2010 | Weeber et al. |

(56) References Cited

U.S. PATENT DOCUMENTS

| | | |
|---|---|---|
| 2010/0157240 A1 | 6/2010 | Schmid et al. |
| 2010/0161048 A1 | 6/2010 | Schaper, Jr. |
| 2010/0188636 A1 | 7/2010 | Pinto et al. |
| 2011/0149236 A1 | 6/2011 | Weeber |
| 2011/0153014 A1 | 6/2011 | Zhang et al. |
| 2011/0279912 A1 | 11/2011 | Fiala |
| 2012/0277857 A1 | 11/2012 | Purchase et al. |
| 2013/0013060 A1 | 1/2013 | Zadno-Azizi et al. |
| 2013/0211515 A1 | 8/2013 | Blum et al. |
| 2013/0226294 A1 | 8/2013 | Van Der Mooren et al. |
| 2015/0250583 A1 | 9/2015 | Rosen et al. |
| 2015/0250585 A1 | 9/2015 | Rosen et al. |
| 2015/0265399 A1 | 9/2015 | Rosen et al. |
| 2015/0297342 A1 | 10/2015 | Rosen et al. |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1424049 A1 | 6/2004 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | 9222264 A1 | 12/1992 |
| WO | 9303409 A1 | 2/1993 |
| WO | 0019906 A1 | 4/2000 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03009053 A1 | 1/2003 |
| WO | WO-03000154 A2 | 1/2003 |
| WO | WO-03022137 A2 | 3/2003 |
| WO | 2004034129 A1 | 4/2004 |
| WO | 2004049979 A1 | 6/2004 |
| WO | 2004068214 A1 | 8/2004 |
| WO | 2004090611 A2 | 10/2004 |
| WO | 2004096014 A2 | 11/2004 |
| WO | 2005019906 A1 | 3/2005 |
| WO | 2006025726 A1 | 3/2006 |
| WO | 2006047698 A1 | 5/2006 |
| WO | 2006060477 A2 | 6/2006 |
| WO | 2006060480 A2 | 6/2006 |
| WO | 2007092948 A1 | 8/2007 |
| WO | 2007133384 A2 | 11/2007 |
| WO | 2008045847 A2 | 4/2008 |
| WO | WO-2008065362 A1 | 6/2008 |
| WO | 2009076670 A1 | 6/2009 |
| WO | WO-2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

Buralli D.A., et al., "Optical Performance of Holographic Kinoforms," Applied Optics, 1989, vol. 28 (5), pp. 976-983.

International Search Report and Written Opinion for Application No. PCT/US2014/020343, mailed on May 15, 2014, 10 pages.

Jafari-Nodoushan M., et al., "Control-Flow Checking Using Branch Instructions," IEEE/IFIP International Conference on Embedded and Ubiquitous Computing, 2008, pp. 66-72.

Morris G.M., et al., Diffractive Lenses for Vision Correction, Apollo Optical Systems LLC, Rochester, NY, USA, 2006.

Oh N., et al., "Control-Flow Checking by Software Signatures," IEEE Transactions on Reliability, 2002, vol. 51 (2), pp. 111-122.

Alfonso J.F. et al., "Prospective Study of the Acri.LISA Bifocal Intraocular Lens," Journal of Cataract Refractive Surgery, 2007, vol. 33(11), pp. 1930-1935.

Canovas C., et al., "Hybrid Adaptive-Optics Visual Simulator," Optical Letters, 2010, vol. 35(2), pp. 196-198.

Cohen A.L., "Practical Design of a Bifocal Hologram Contact Lens or Intraocular Lens," Applied Optics, 1992, vol. 31 (19), pp. 3750-3754.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, 1992, vol. 1780, pp. 393-402.

Escudero-Sanz I., et al., "Off-Axis Aberrations of a Wide-Angle Schematic Eye Model," J Opt Soc Am A Opt Image Sci Vis., 1999, vol. 16(8), pp. 1881-1891.

Hoffmann, P.C., et al., "Analysis of Biometry and Prevalence Data for Corneal Astigmatism in 23 239 Eyes," Journal of Cataract and Refractive Surgery, 2010, vol. 36(9), pp. 1479-1485.

International Search Report and Written Opinion for Application No. PCT/IB2015/000989, mailed on Sep. 8, 2015, 13 pages.

International Search Report and Written Opinion for Application No. PCT/IB2015/001027, mailed on Sep. 8, 2015, 14 pages.

International Search Report and Written Opinion for Application No. PCT/IB2015/001244, mailed on Nov. 8, 2015, 14 pages.

International Search Report and Written Opinion for Application No. PCT/IB2015/001588, mailed on Oct. 15, 2015, 11 pages.

International Search Report and Written Opinion for Application No. PCT/IB2015/002000, mailed on Feb. 12, 2016, 12 pages.

International Search Report and Written Opinion for Application No. PCT/US2012/052311, mailed on Dec. 21, 2012, 14 pages.

Jaeken B., et al., "Comparison of the Optical Image Quality in the Periphery of Phakic and Pseudophakic Eyes," Investigative Ophthalmology &, Visual Science, 2013, vol. 54 (5), pp. 3594-3599.

Liou H.L., et al., "Anatomically Accurate, Finite Model Eye for Optical Modeling," Journal of Optical Society of America, 1997, vol. 14 (8), pp. 1684-1695.

Marsack J.D., et al., "Metrics of Optical Quality Derived from Wave Aberrations Predict Visual Performance," Journal of Vision, 2004, vol. 4 (4), pp. 322-328.

Monsoriu J.A., et al., "Devil's Lenses," Optics Express, 2007, vol. 15 (21), pp. 13858-13864.

Norrby S., et al., "Model Eyes for Evaluation of Intraocular Lenses," Applied Optics, 2007, vol. 46 (26), pp. 6595-6605.

Piers P.A., et al., "Eye Models for the Prediction of Contrast Vision in Patients with New Intraocular Lens Designs," Optics Letters, 2004, vol. 29 (7), pp. 733-735.

Piers P.A., et al., "Theoretical Comparison of Aberration-Correcting Customized and Aspheric Intraocular Lenses," Journal of Refractive Surgery, 2007, vol. 23 (4), pp. 374-384.

Shammas, J.H., "Intraocular Lens Power Calculations," Chapter 12, "Ultrasound Measurement of the Challenging Eye," Slack Incorporated, p. 117, Copyright 2004.

Siedlecki D., et al., "Radial Gradient index Intraocular Lens: a Theoretical Model," Journal of Modern Optics, 2008, vol. 55 (4-5), pp. 639-647.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

Van Den Berg T.J., "Analysis of Intraocular Straylight, Especially in Relation to Age," Optometry and Vision Science 1995, vol. 72 (2), pp. 52-59.

Van Meeteren A., "Calculations on the Optical Modulation Transfer Function of the Human Eye for White Light," Optica Acta, 1974, vol. 21(5), pp. 395-412.

Villegas E.A., et al., "Correlation between Optical and Psychophy, Sical Parameters as a Function of Defocus," Optometry and Vision Science, 2002, vol. 79 (1), pp. 60-67.

(56) References Cited

OTHER PUBLICATIONS

Baskaran K., et al., "Benefit of Adaptive Optics Aberration Correction at Preferred Retinal Locus," Optometry and Vision Science, 2012, vol. 89 (9), pp. 1417-1423.
Lewis P., et al., "Resolution of Static and Dynamic Stimuli in the Peripheral Visual Field," Vision Research, 2011, vol. 31 (16), pp. 1829-1834.
Lundstroma L, et al., "Symmetries in Peripheral Ocular Aberrations," Journal of Modem Optics, 2011, vol. 58 (19-20), pp. 1690-1695.
Rosen R., et al., "Adaptive Optics for Peripheral Vision," Journal of Modem Optics, 2012, vol. 59 (12), pp. 1064-1070.
Rosen R., et al., "Evaluating the Peripheral Optical Effect of Multifocal Contact Lenses," Ophthalmic and Physiological Optics, 2012, vol. 32 (6), pp. 527-534.
Rosen R., et al., "Have We Misinterpreted the Study of Hoogerheide Et Al. (1971)?," Optometry and Vision Science, 2012, vol. 89 (8), pp. 1235-1237.
Rosen R., et al., "Sign-dependent Sensitivity to Peripheral Defocus for Myopes Due to Aberrations," Investigative ophthalmology & Visual Science, 2012, vol. 53 (11), pp. 7176-7182.
Rosen R., et al., "Influence of Optical Defocus on Peripheral Vision," Visual Psychophysics and Physiological Optics, 2011, vol. 52 (1), pp. 318-323.
Rosen R., "Peripheral Vision: Adaptive Optics and Psychophysics," Doctoral Thesis Department of Applied Physics Royal Institute of Technology Stockholm, Sweden 2013, 86 pages.

INTRAOCULAR LENS THAT MATCHES AN IMAGE SURFACE TO A RETINAL SHAPE, AND METHOD OF DESIGNING SAME

CROSS-REFERENCES TO RELATED APPLICATIONS

This application claims priority to U.S. provisional application No. 61/776,184 filed on Mar. 11, 2013, the entire contents of which are incorporated herein by reference.

FIELD OF THE INVENTION

The present disclosure relates to intraocular lenses (IOLs), and more particularly to IOLs designed to produce an image surface that matches the curved surface of the retina.

BACKGROUND OF THE INVENTION

When light from an object in the field of view of a human subject's eye enters the eye through the pupil, the light is focused by refraction through the optical system of the eye onto the retina, forming an image of the object on the retina. Photoreceptor cells in the retina react to the light and send signals through the optic nerve to the brain, where the signals are perceived as the object in the visual field. The photoreceptor cells are not uniformly distributed on the retina, and the resolution of the perceived object is determined in part by the density of the photoreceptors at the location on the retina where the image of that object is formed. The resolution of the perceived object is also determined in part by how correctly the image is focused on the retina by the eye's optical system. The eye's refracting optical elements include the cornea and the lens. If those elements are not able to focus on the retina, the image formed will be distorted and the subject's vision will not be optimal.

The photoreceptor cells in the retina that detect light are called rods and cones. The cone cells, named for their conical shape, function best in relatively bright light and are responsible for detecting color. The cones are most densely packed near a point on the retina called the fovea, and become less dense moving away from the fovea. The fovea is a small pit-like structure disposed near the central axis of the optics of the eye. Thus, the cones are responsible for high resolution vision of well-lit objects in the center of the visual field. In contrast, the rod cells, named for their cylindrical shape, function well in dim light and are most densely concentrated at the periphery of the retina, becoming less dense moving toward the fovea. The rods thus provide for peripheral vision and night vision.

In a healthy eye, light from the center of the field of view enters the pupil and is sharply focused near the fovea, whereas light from the periphery of the field of view is focused at corresponding points on the periphery of the retina. However, any of a plurality of disorders can cause the optics of the eye to focus light improperly on the retina, causing the subject's vision to be blurred.

To resolve some disorders, such as clouding that develops in the eye lens (called a "cataract"), the natural lens may be surgically removed, and an intraocular lens (IOL) surgically implanted in the eye, typically placed at the former location of the natural lens of the eye.

IOLs are designed to work in conjunction with the optical elements of the eye (e.g., the cornea) to produce a sharp image only at the on-axis focal point on the retina and the paraxial region centered thereon. In general, no consideration is given to the off-axis optical properties of the retina or the optical system. Accordingly, even when a subject's vision is corrected at the center of the visual field, the peripheral image in general remains out of focus, resulting in a retinal image that is not optimal. As such, the subject's corrected vision is not as good as it could be, and peripheral vision and night vision are generally much worse than optimal.

Moreover, prior art IOLs do not correct any form of central vision loss, because the only portion of the retinal image that is in focus is located at the point where central vision occurs, i.e., where the central axis of the optics of the eye intersects the retina. In addition, some disorders involve changes in the retinal surface topography, such as substance buildup in the outer retina. Because prior art IOLs only focus light near the fovea, they do not correct for such changes in the diseased peripheral retinal surface.

BRIEF DESCRIPTION OF THE FIGURES

Understanding of the herein described devices, systems, and methods will be facilitated by consideration of the following detailed description of the preferred embodiments in conjunction with the accompanying drawings, in which like numerals refer to like parts. In the drawings.

SUMMARY

The present invention is and includes an intraocular lens (IOL), system, and method. The IOL, system and method may include having a base lens and a complementary lens selected to form a curved image surface matching a retina surface when placed in an eye's line of sight.

DETAILED DESCRIPTION

It is to be understood that the figures and descriptions provided herein may have been simplified to illustrate elements that are relevant for a clear understanding of the present invention, while eliminating, for the purpose of clarity, other elements found in typical vision correcting lenses, lens systems, and methods. Those of ordinary skill in the art may recognize that other elements and/or steps may be desirable and/or necessary to implement the devices, systems, and methods described herein. However, because such elements and steps are well known in the art, and because they do not facilitate a better understanding of the present invention, a discussion of such elements and steps may not be provided herein. The present disclosure is deemed to inherently include all such elements, variations, and modifications to the disclosed elements and methods that would be known to those of ordinary skill in the pertinent art.

The present disclosure describes a compound-lens IOL that may be part of an optical system and method, and that may, alone or in the optical system and method, match an image surface shape to the shape of an eye's retina. The IOLs, systems, and methods disclosed herein provide improved vision, including improved peripheral vision and night vision.

The disclosure also describes surgically implantable intraocular elements, contact lenses, spectacle lenses, and corneal inlays, as well as corneal reshaping procedures and combinations of the foregoing, and may provide the aforementioned matching. The present invention may also include other refractive corrections, such as accommodating ophthalmic corrections, higher order aberration corrections, adjustable refractive corrections, and multifocal refractive corrections, by way of non-limiting example, and that may also provide the aspects described herein.

The herein described devices, systems, and methods match an image surface to the shape of the retina. In particular, one or more intraocular lenses are used to achieve a desired image surface that matches the curved surface of the retina. Thereby, the subject's vision in well-lit environments is substantively improved over the prior art. In addition, the subject's peripheral vision and vision in dimly lit environments are dramatically improved.

Figure 1:
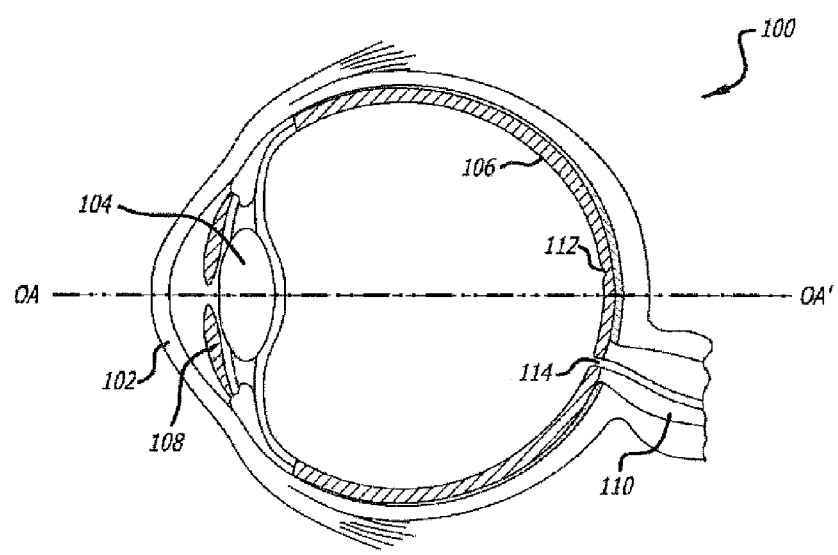
FIG. 1 is a simplified diagram of a healthy eye.

FIG. 1 illustrates a normal eye 100, including cornea 102, lens 104, and retina 106. Light emanating from or reflecting off of objects in the eye's field of view enters the eye through the cornea, and is refracted by the cornea. The light then passes through an aperture in the center of iris 108, called the pupil. The iris is opaque, and forms a stop to block light not passing through the pupil. The light passed then proceeds through lens 104. The lens adjusts its shape in a manner that focuses the light onto the surface of retina 106, forming an image thereon. These structures of the eye form an optical system with a central optical axis, OA-OA', that intersects the retina near fovea 112.

Figure 2:
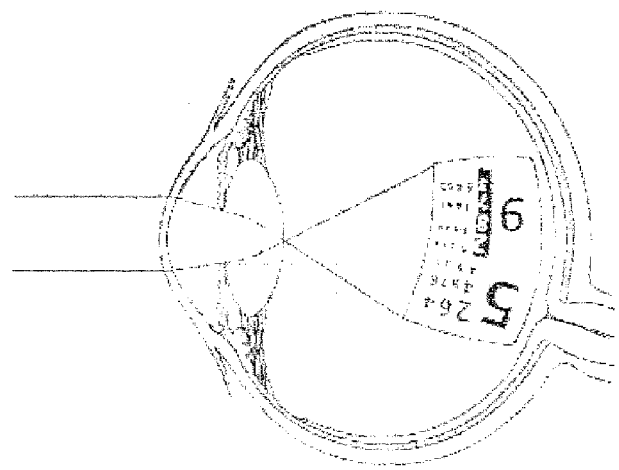
FIG. 2 illustrates an image formed in a healthy eye, with a shape that matches the shape of the retina.

In a normal eye, the lens focuses light from objects in the entire field of view onto the curved surface of retina 106, forming an image of the visual field thereon. Photoreceptor cells in the retina react to the light and send signals through optic disc 114 (the "blind spot") to optic nerve 110, and thence to the brain (not shown). The optic disc represents the beginning of the optic nerve 110 to the brain. In the brain, the signals are perceived as the objects in the visual field. FIG. 2 illustrates an image being formed on the retina surface by the natural lens, wherein the image surface matches the shape of the retina surface.

During cataract surgery an IOL is surgically implanted in the subject's eye, typically at the location at which the natural lens resided. An IOL is made of a refractive material, and is designed to focus light entering the eye onto the retina.

In general a single IOL is used, and it is designed so that the field of view is in focus only at the point at which the central axis of the optical system of the eye intersects the retina, while ignoring the off-axis properties of the eye and its optical system. The result leads to suboptimal vision, due at least to uncorrected field curvature and oblique astigmatism of the cornea/lens system, also known as marginal or radial astigmatism.

Figure 3:
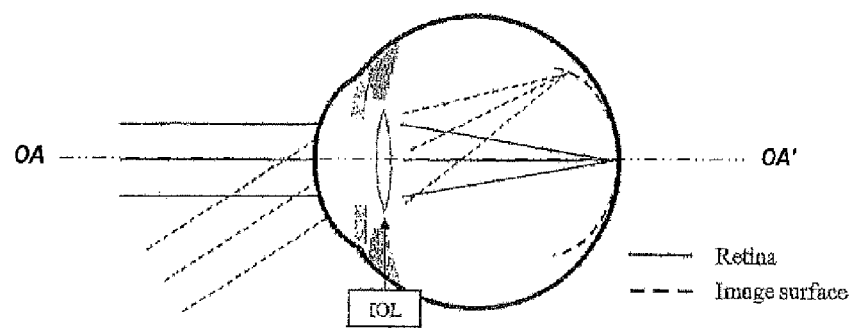
FIG. 3 illustrates the difference between the shape of the image surface and the surface of the retina.

FIG. 3 illustrates the typical situation where the IOL is designed to focus light entering the eye from the left (as shown) through the cornea onto the retina. The prior art practice is to design the IOL to focus light only at a single point, where the central axis of the optical system, including the cornea and IOL, intersects the retina, and thereby the off-axis properties of both the optical system and the retina are ignored. As illustrated in FIG. 3, the image surface forms in front of the retina except where the optical axis intersects it, i.e., the image surface is less flat than the retina (i.e., is "more curved"). In other cases (not shown), the image surface may be formed behind the retina except where the optical axis intersects it, i.e., the image surface is flatter than the retina. As a result, in either case the image formed on the rest of the retina is blurred.

Compound lenses comprising a plurality of lens elements can be used to correct for these effects. However, prior art compound lenses are typically designed to provide an image surface that is flat, not curved. For example, imaging devices such as film, charged couple devices (CCDs), etc. that used in cameras, telescopes, microscopes, and the like have a flat (i.e., not curved) surface on which the image is formed. The surface on which etched components are formed by focusing light with compound lenses in semiconductor manufacturing is also flat. Accordingly, the compound lenses for use in such applications are typically designed to form a flat image. In contrast, the image surface produced by the herein disclosed devices, systems, and methods is curved to match the curved surface of the actual retina of a particular subject's measured eyeball.

Retinal shapes vary greatly between individuals. For example, different refractive groups, such as those with myopia (nearsighted) and those with hyperopia (farsighted), have been determined to have generally different retinal shapes (see, e.g., Atchison D A, Pritchard N, Schmid K L, Scott D H, Jones C E, Pope J M, *Shape Of The Retinal Surface In Emmetropia And Myopia*, Invest Ophthalmol Vis Sci 2005, 46:2698-2707, the entirety of which is incorporated herein as if fully set forth). Therefore biometry, including measuring the dimensions and retinal shape of a particular subject's eye, must be carried out before implanting an IOL. Preferably, such biometry can be performed using one or more of Optical coherence tomography (OCT), confocal Scanning Laser Ophthalmoscopy (cSLO), Magnetic resonance imaging (MRI), and the like. Once the biometry has been completed and the eye dimensions and retinal shape are known, IOLs can be selected or designed that will form an image surface that matches the shape of the retina surface of the measured eye.

The image surface of an optical system is determined by the tangential and sagittal surfaces arising from oblique astigmatism, together with field (Petzval) curvature. In embodiments, two or more lenses can be incorporated into the IOL design to account for this image surface. Depending on the image shape desired to be formed, different combinations of lenses having positive and negative powers can be incorporated into the IOL design. The Petzval surface for a positive lens (i.e., a convex lens) bends inward, while that of a negative lens (i.e., a concave lens) bends outward. Thus, positive and negative lenses can be combined into a single compound IOL or IOL system that matches the image surface to the measured retina surface.

Figure 4:
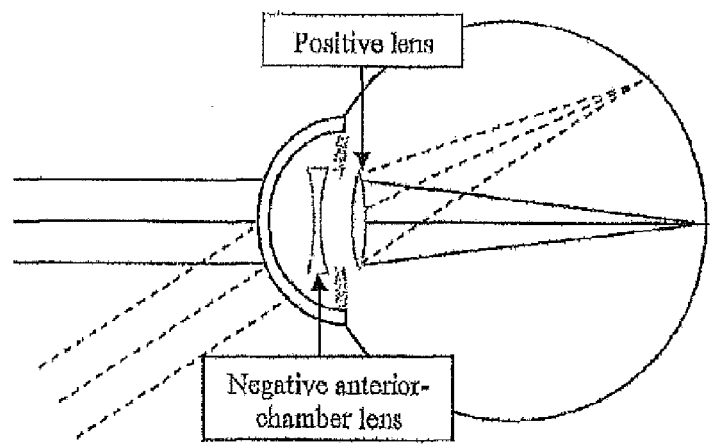
FIG. 4 illustrates the image surface shape being matched to the retinal surface shape in accordance with the disclosure.

In an exemplary method of selecting or designing an IOL or IOL system, a desired IOL power is calculated for a particular measured eye in accordance with well-known prior art practices. Then, a positive lens may be selected to be positioned, for example in the posterior chamber, and a negative lens may be selected to be positioned, for example, in the anterior chamber. Such a configuration is illustrated in FIG. 4. The positive and negative lenses are selected to have a combined power equal to the IOL power calculated for the eye's deficiencies. In addition, the lenses are selected to achieve a particular Petzval surface radius that matches that of the retinal surface. The expression for the Petzval curvature is:

$$\frac{1}{R_p} = -n_N \sum_{i=1}^{N} \frac{n_i - n_{i-1}}{n_i n_{i-1} R_i}$$

where $R_p$ is the Petzval radius of curvature, and $R_i$ and $n_i$ are the radius of curvature and refractive index, respectively, of the $i^{th}$ lens surface of the combined IOL lenses. It is desired to match $R_p$ to the radius of curvature of the subject's measured eye. To do so, lenses are selected with lens surfaces that have $R_i$ and $n_i$ which, when combined in accordance with the equation above, result in the desired Petzval radius.

In an exemplary operation, a subject's eye is measured, and it is determined that the retina's radius of curvature is about 17.0 mm, and the corneal anterior radius of curvature is about 7.8 mm, and the corneal posterior radius of curvature is about 6.4 mm. The cornea has a refractive index of 1.375. In accordance with standard prior art practices, it is determined that a standard 20 diopter (20 D) positive monofocal IOL results in the desired focus at the central optical axis on the retina. In addition, the optical system of the eye, including the cornea and the standard 20 D IOL, is determined to have a Petzval radius of about −17.7 mm, i.e., larger than the radius of curvature of the retina. This results in an image surface that is somewhat flatter than the measured retinal shape. Therefore, the image formed on the retina is out of focus except at the paraxial region. To match the image surface to the retinal surface so that the image formed is in focus everywhere on the retina, the Petzval radius of the optical system must be reduced.

To reduce the Petzval radius, the single standard IOL of the prior art can be replaced with two lenses. One lens is a positive lens that is stronger than 20 D, and is designed or selected (hereinafter collectively referred to as "selected") for implantation at a select position in the posterior chamber. A second, negative lens is selected for implantation at a select position in the anterior chamber. The two lenses properly configured will result in an effective power of 20 D as before, but will have a Petzval radius of −17.0 mm so that the image surface matches the retinal surface. For example, a positive 40 D IOL may be selected for placement in the posterior-chamber, and a negative IOL may be selected for placement in the anterior chamber such that the resulting optical system has a Petzval radius of about −17.0 mm.

In the case where the Petzval surface's radius of curvature is smaller than the radius of curvature of the retinal surface, the opposite approach may be used. In an exemplary operation suitable for this case, a subject's eye is measured and it is again determined that the retina's radius of curvature is about 19.0 mm. As before, in accordance with standard prior art practices it may be determined that a standard 20 diopter (20 D) positive monofocal IOL results in the desired focus at the central optical axis on the retina. In this case, however, the optical system of the eye, including the cornea and the standard 20 D IOL, is determined to have a Petzval radius of about −18.3 mm. This results in an image surface that is less flat than the measured retinal shape, as illustrated in FIG. 3. The image formed on the retina is again out of focus except for the paraxial region. But in this case, to match the image surface to the retinal surface so that the image formed is in focus everywhere on the retina, the Petzval radius of the optical system must be increased.

To increase the Petzval radius, the single standard IOL can be replaced with two lenses. One lens is a positive lens that is weaker than 20 D, and is selected for implantation at a select position in the posterior chamber. A second positive lens is selected for implantation at a select position in the anterior chamber. The two lenses properly configured will result in an effective power of 20 D as before, but will have a Petzval radius of −19.0 mm so that the image surface matches the retinal surface. For example, a positive 10 D IOL may be selected for placement in the posterior-chamber, and a second positive IOL may be selected for placement in the anterior chamber such that the resulting optical system has a Petzval radius of about −19.0 mm.

Thus, in either case, two IOLs may be selected which, when properly configured, result in a Petzval radius that matches the shape of the retina. This assumes that the shape of the retina is such that it can be matched with only two lenses. Some more complicated retinal shapes may be matched using more elaborate optical systems comprising more than two lenses, and/or non-spherical lenses, or lenses formed with bumps or depressions disposed so that the resulting image surface formed matches the surface of the retina, as will be appreciated by those skilled in the art in light of the disclosure herein.

In various embodiments, one or more of the plurality of IOLs used may be fully refractive, fully diffractive (see, e.g., Morris G M, Buralli D A, Federico R J. *Diffractive Lenses For Vision Correction*. USA: Apollo Optical Systems, LLC, Rochester, N.Y. 2006, the entirety of which is incorporated herein as if fully set forth), or have a combination of diffractive and refractive surfaces (i.e., a hybrid lens). Selecting appropriate combinations of refractive, diffractive, and/or hybrid lenses can extend the range of shapes to which an image surface can be tuned. Notably, unlike the fully refractive lenses commonly used in IOLs, which always have a curved image surface, diffractive lenses can have a flat image surface (see, e.g., Buralli D A, Morris G M, Rogers J R, *Optical Performance Of Holographic Kinoforms*, Appl Opt 1989; 28:976-983, the entirety of which is incorporated herein as if fully set forth). Accordingly, using one or more diffractive surfaces on one or more of the lenses can enhance the range of retina surface shapes that can be matched.

Various embodiments include compound lenses in which a plurality of optical system characteristics may be modified to achieve an image surface that matches the shape of a particular measured retina. These characteristics can include, with regard to each lens: selecting a size, shape, and thickness of the lens; selecting each surface of the lens to be refractive or diffractive; selecting an index of refraction of a homogeneous material from which the lens is formed, or forming the lens from a material having one or more refraction index gradients, each gradient extending smoothly or in discrete steps from a low value to a high value; selecting a distance of the lens along the optical axis from a fixed point on the axis such as a surface of the cornea or the retina; selecting an orientation of each surface of the lens about the optical axis in a plane normal (perpendicular) to the optical axis; placing the lens in a select plane that is not normal to the optical axis, or using a lens having a surface that is not normal to the optical axis; or any other physical characteristic of the lens or its placement in the system. The characteristics can also include, with regard to combining a plurality of lenses: selecting a number of lenses to combine;

selecting an order of the lenses from the cornea to the retina or vice versa; or any other physical characteristic of the lens system or its placement.

In an embodiment, once the IOL system is designed, each IOL of the system is individually implanted in the eye. In another embodiment, a plurality of lenses may be combined to form a single compound IOL unit, such as an enclosure or envelope that contains a plurality of lens elements the entirety of which can be implanted together. Such an enclosure can include structural elements to secure each lens element's position and orientation within the enclosure. Such a compound IOL can be inserted in a single operation into the capsular bag after the natural lens is removed. Further, one or more IOLs or compound IOLs may be used in conjunction with a non-implanted, i.e., an exterior, lens or lenses.

In various embodiments, the calculations performed to design an optical system that matches the shape of a retina can be simplified by standardizing at least some of the parameters of the optical system, and preferably as many parameters as is practicable to achieve an acceptable result. An acceptable result may be determined by how closely the image surface formed by the optical system matches the measured shape of the retina. In an exemplary embodiment, an IOL system may be designed with first and second discrete IOL elements that may be individually implanted in the eye. The first IOL may be a positive lens disposed at a "standard" location within the posterior chamber and formed of a homogeneous material having a "standard" index of refraction. The second lens may be disposed at a "standard" location within the anterior chamber, and may be formed of a homogeneous material. No diffracting surfaces, surfaces tilted from the optical axis, surfaces with bumps or depressions, or the like may be used in this example. In this simplified case, the parameters of the first lens that must still be selected include its height, width, shape, thickness at the center of the lens, and the radii of curvature of its two surfaces. The second IOL may be either positive or negative, and its height, width, shape, thickness at the center of the lens, and the radii of curvature of its two surfaces must also be selected. The second lens may also be formed of a material having the same index of refraction as the first lens. However, it is noted that the Petzval radius of curvature of a lens depends not only on the radius of curvature of each of its surfaces, but on the lens' refractive index as well. Consequently, the range of Petzval radii that can be achieved by using the second lens, and hence by the entire optical system, can be extended by selecting a homogenous material for the second lens having a higher or lower refractive index than the material of the first lens.

In an embodiment, all lenses can be placed in the posterior chamber inside the capsular bag. It is noted that an IOL system having two optical components is described in U.S. Pat. No. 7,238,201, entitled ACCOMMODATING INTRAOCULAR LENS SYSTEM WITH ENHANCED RANGE OF MOTION, the entirety of which is hereby incorporated by reference as if fully set forth. That system comprises an anterior optic and a posterior optic coupled to anterior and posterior haptic arms, respectively. The '201 patent relates to other than the matching of the image surface to the shape of the retina that is included the herein disclosed devices, systems, and methods. Rather, the haptic arms are arranged so that a forward movement of the posterior optic actuates a substantially larger forward movement in the anterior optic. This supports the ability of the eye to modify its refractive power when viewing objects at different distances, called "accommodation". Nevertheless, in an embodiment, the shape and power of each optic in such a system may be selected to achieve a Petzval surface that matches the shape of the retina in accordance with the present disclosure.

In another embodiment, one lens may be placed in the anterior or posterior chamber, and the other lens may be a surface profile disposed on or within the cornea, the surface profile having been formed by a laser, (e.g., using a LAW, LASEK, or PRK procedure) resulting in the reshaping of the cornea.

Figure 5:
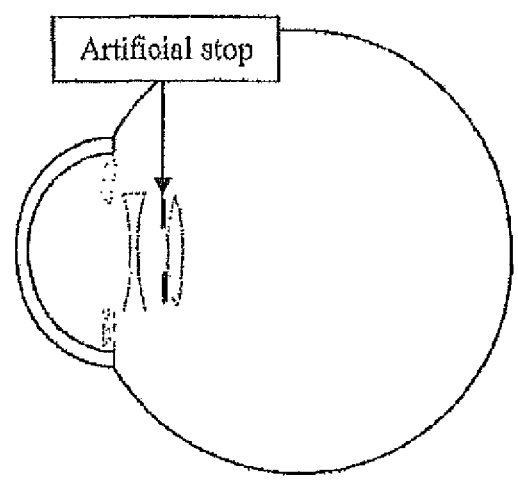
FIG. 5 illustrates an embodiment of an optical system in accordance with the disclosure.

As shown in FIG. 5, in an embodiment an aperture can be added to the optical system as an artificial stop, such that it is the limiting aperture of the optical system of the eye instead of the pupil. Adding the aperture does not affect the Petzval surface. However, oblique astigmatism can be improved by selecting an appropriate stop size and position.

Figure 6:
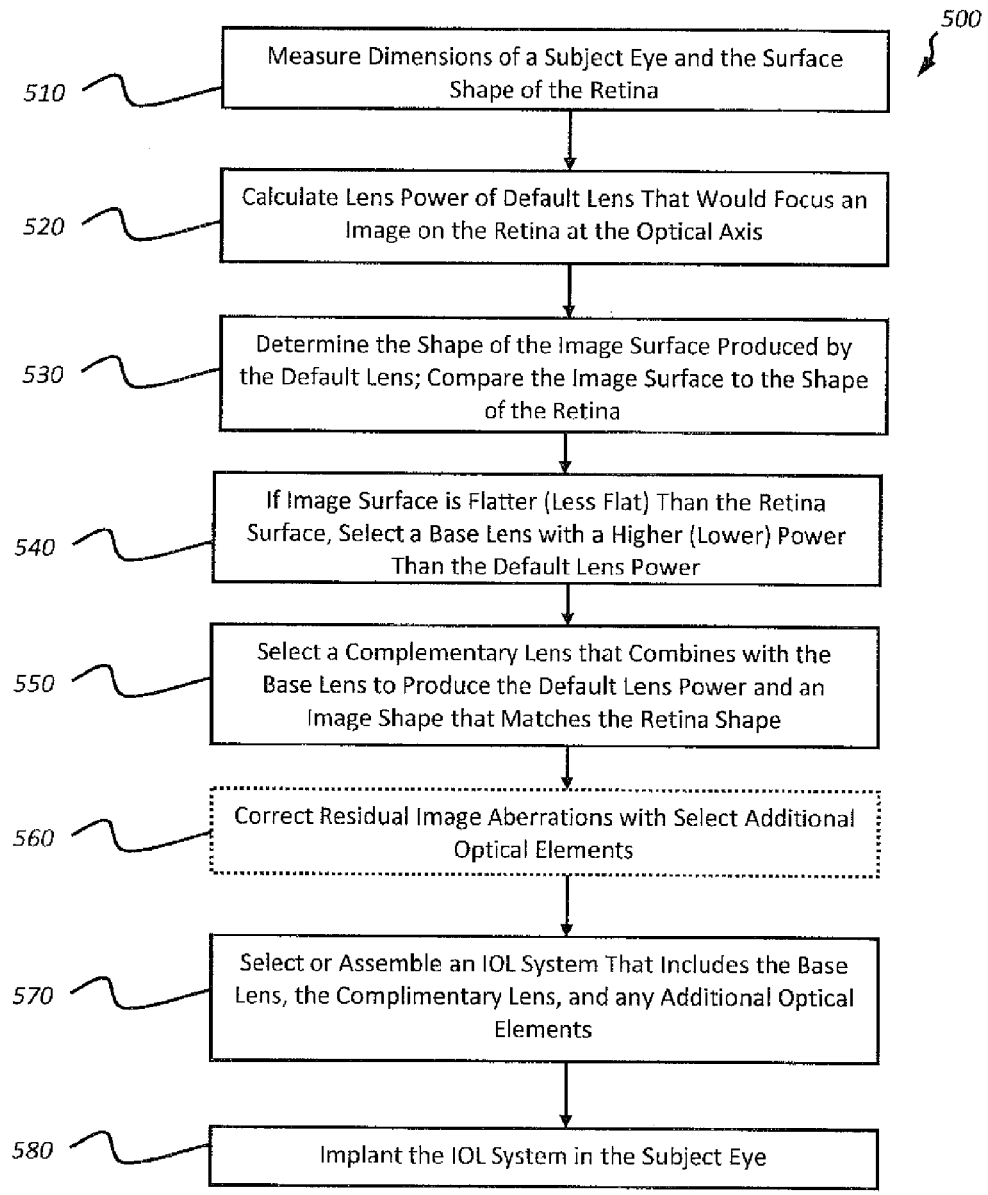
FIG. 6 illustrates a method of matching an image surface shape to an retinal shape in accordance with the disclosure.

Referring now to FIG. 6, there is shown a method 500 for matching an optical system image surface to the surface of a retina. Method 500 includes measuring the dimensions of a subject eye and the shape of the surface of its retina, 510. The lens power needed to focus an image at the intersection of the optical axis of the eye on the retina is calculated, 520. The shape of the image surface produced at the retina by that lens can then be determined and compared to the shape of the retina, 530. In the case where the image surface is flatter than the retina surface, a base lens power may be selected that has a higher power than the default lens power, 540. In that case, a negative complementary lens may be selected or designed that adjusts the image shape of the optical system to match the retina shape, 550. Conversely, in the case where the image surface is less flat (i.e., more curved) than the retina surface, a base lens power may be selected that has a lower power than the default lens power, 540. In that case, a positive complementary lens may be selected or designed that adjusts the image shape of the optical system to match the retina shape, 550. If needed, additional optical elements may be selected, for example, to correct any residual image aberrations, 560. An IOL system can then be selected or assembled that includes the base lens, the complimentary lens, and any additional optical elements, 570. The IOL system can then be implanted in the subject eye, 580.

Figure 7:
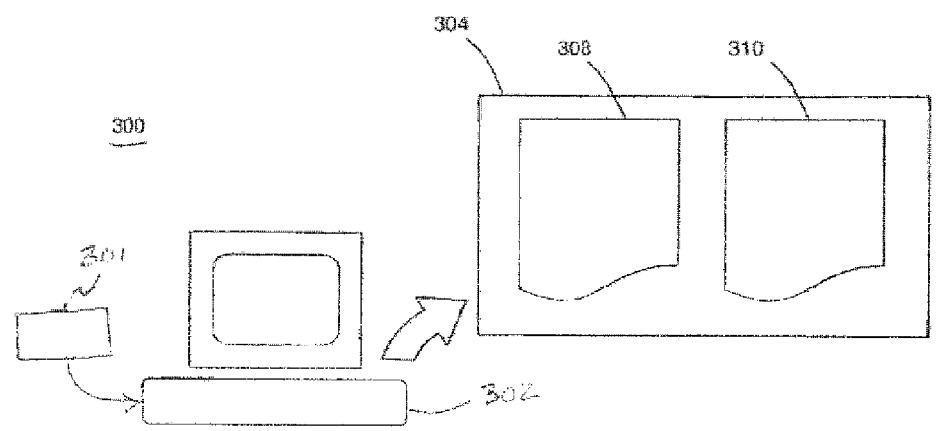
FIG. 7 is a simplified diagram of a system for carrying out the method shown in FIG. 6, in accordance with the disclosure.

As illustrated in FIG. 7, the present invention may be implemented using a clinical system 300 that is capable of assessing the eye's biometry and of performing the calculations set forth in method 500. The system 300 may include a biometric reader 301, a computing processor 302, and a computer readable storage device 304 in data communication with the processor 302. The computer readable storage device may include a volatile or non-volatile memory, a magnetic or optical drive, or the like. Storage device 304 may store therein an array of values 308 such as properties of various optical elements in various configurations. The storage device may also store therein sequences of instructions 310 which, when executed by the processor 302, cause the processor 302 to select or design an IOL system configured for implantation into the eye of the subject presenting the biometric readings to biometric reader 301. The array of values 308 may comprise data used or obtained from method 500 or other methods consistent with embodiments of the invention. The sequence of instructions 310 may include one or more steps of method 500 or other methods consistent with embodiments of the invention.

The processor 302 may be embodied in a general purpose computer, such as a desktop or laptop computer, and/or the processing, storage, and/or other resources of a computing cloud accessible through a network. The processor 302 may comprise or be coupled to hardware associated with biometric reader 301 operable to select or design an IOL system for placement into the eye of the subject that matches an image shape to the retina shape. In embodiments, the system 300 may be configured to be coupled to or receive data from another device, such as one or more instruments for obtaining measurements of a subject eye. Alternatively, the system 300 may be embodied in a handheld device that may be adapted to be electronically and/or wirelessly coupled to one or more other devices.

In another embodiment, rather than using a dual lens system, a single lens may be used with two different refractive indeces. In the thin lens approximation with lenses placed tightly together, the Petzval sum is $P1/n1+P2/n2+\ldots$, where P is equal to power. In a single lens embodiment, one part of the lens may be comprised of a high refractive index and another part of the lens comprised of a low refractive index. By way of example, the anterior or posterior part of the lens may have a high refractive index and the opposing side may have a low refractive index. Refractive power can then be appropriately distributed to make the Petzval surface of the IOL plus the cornea match the retina.

In certain embodiments a single lens, single refractive index material may be used. Certain 101 designs rely on having a well-defined shape factor. Additionally, the power is determined to give optimal focus on the fovea. However, if the lens is designed with enough thickness, preferably in the shape of a meniscus lens, the Petzval curvature may be optimized to match the retinal radius of curvature. The procedure for designing such a lens may comprise of:

1) receiving a measurement of at least a shape of a retina of a subject eye, wherein the retina has a radius of curvature;

2) determining a desired shape factor for an IOL, wherein the shape factor is determined from optical factors, engineering constraints and/or anatomical constraints;

3) determining a total IOL power for focusing light onto the retina surface of the subject eye;

4) determining the power of each respective surface of the IOL from a thickness of the IOL, the desired total IOL power and the desired shape factor; and 5) comparing a Petzval sum to the retinal radius of curvature. If the Petzval sum does not match the retinal radius, the power of the two surfaces may be increased or decreased. This adjustment of the power of the surfaces may be done while keeping the shape factor constant. The change of surfaces will change the power of the IOL, so the thickness of the IOL may be adjusted to correct the power. This adjustment of IOL thickness does not impact the Petzval sum or the shape factor. An advantage of this embodiment is that a single refractive index material may be used.

Although the invention has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

The invention claimed is:

1. A method of matching an image surface to a retina surface, comprising:
   receiving a measurement of at least a shape of a retina of a subject eye;
   determining a lens power that would focus light passing through the cornea and the pupil of the subject eye onto the retina surface;
   determining a shape of an image surface that would be produced by the eye with an IOL having the lens power;
   comparing the image surface shape to the shape of the retina surface;
   selecting a base lens power, including:
      in the case the image surface is flatter than the retina surface, selecting a base lens power greater than the lens power;
      in the case the image surface is less flat than the retina surface, selecting a base lens power less than the lens power;
   calculating a complimentary lens power equal to the lens power minus the selected base lens power; and
   providing for insertion in the subject eye's line of sight a base lens having the base lens power and a complementary lens having the complementary lens power.

2. The method of claim 1, wherein the base lens and the complementary lens are provided for insertion individually.

3. The method of claim 1, further comprising assembling a compound IOL that includes the base lens and the complementary lens, whereby the insertion of the base lens and the complementary lens is achieved by implanting the compound IOL.

4. The method of claim 3, wherein the compound IOL is assembled using components selected from a plurality of preformed base lenses and a plurality of preformed complementary lenses.

5. The method of claim 3, wherein the compound IOL is selected from a plurality of pre-formed compound IOLs.

6. The method of claim 1, further comprising selecting at least one additional optical element for the compound IOL to correct image aberration.

7. The method of claim 6, wherein the additional optical element is an aperture.

8. The method of claim 1, wherein the providing for insertion includes providing for a surgical modification of the cornea of the eye.

9. A system for specifying a plurality of intraoptical lenses that combine to form an image shape matched to a retina surface, comprising:
   biometric apparatus operable to measure the dimensions and retina shape of an eye and to produce measurement data thereof;
   a computing processor operable to receive the measurement data from the biometric apparatus; and
   a non-transitory data storage device in data communication with the processor and storing therein information of a plurality of IOL lenses and instructions which, when executed on the processor, cause the system to:
   determine a lens power of a default IOL that would focus light passing through the cornea and the pupil of the eye onto the retina according to the measurement data;
   determine a shape of an image surface that would be produced by the eye with the default IOL;
   compare the image surface shape to the shape of the retina;
   select a base lens power, including:
      in the case the image surface is flatter than the retina surface, selecting a base lens power greater than the default IOL lens power; and
      in the case the image surface is less flat than the retina surface, selecting a base lens power less than the default IOL lens power;
   calculating a complimentary lens power equal to the default lens power minus the selected base lens power; and specifying a base lens having the base lens power and a complementary lens having the complementary lens power for implantation in the eye.

* * * * *